United States Patent [19]

Monroe

[11] Patent Number: 5,068,002

[45] Date of Patent: Nov. 26, 1991

[54] ULTRASONIC GLOW DISCHARGE SURFACE CLEANING

[75] Inventor: Marvin E. Monroe, Sunbury, Ohio

[73] Assignee: Quintron, Inc., Galena, Ohio

[21] Appl. No.: 389,308

[22] Filed: Aug. 3, 1989

[51] Int. Cl.$^5$ ............................ B44C 1/22; B08B 3/12
[52] U.S. Cl. ...................................... 156/345; 134/1;
156/627; 156/643; 156/646; 204/192.1;
204/298.31
[58] Field of Search ............... 134/1; 156/345, 643,
156/646, 626, 627; 204/164, 298.1, 298.31,
298.32, 298.34, 298.39, 192.1, 192.32, 192.33

[56] References Cited

U.S. PATENT DOCUMENTS 4,657,616 4/1987 Benzing et al. ................ 134/1 X
4,786,352 11/1988 Benzing .......................... 156/345

Primary Examiner—William A. Powell
Attorney, Agent, or Firm—Frank H. Foster

[57] ABSTRACT

An apparatus is disclosed for abrading contaminants from the surface of a workpiece using plasma glow discharge. The workpieces are positioned in a low pressure chamber with an ionizable gas. A pair of spaced, conductive, interfacing panels form electrodes mounted within the chamber and defining a three-dimensional cleaning space between the electrodes. The electrodes are energized by a power supply, providing an alternative voltage at an ultrasonic frequency and the pressure is maintained to allow only abnormal glow discharge. After initiation of the abnormal glow discharge the electrode current is sensed to detect when to inject additional ionizable gas into the low pressure chamber.

9 Claims, 2 Drawing Sheets

ULTRASONIC GLOW DISCHARGE SURFACE CLEANING

TECHNICAL FIELD

This invention relates generally to the use of ion bombardment from a plasma for cleaning the surfaces of a workpiece, such as a dental implant and more particularly relates to a device of that type which operates at ultrasonic frequencies and has a pair of electrodes within the low pressure chamber to define the cleaning space.

BACKGROUND ART

The bombardment of workpieces with molecular, atomic or subatomic particles has been used for abrading the surfaces of workpieces, for oxidizing surface contaminants or for sterilizing the surface by killing organisms. In such a system an ionizable gas is subjected to an electric or electromagnetic field to free and accelerate electrons. Free electrons gain energy from the imposed electric field and impart this energy through collision with electrically neutral gas molecules to ionize the gas molecules when they collide with them. The collisions produce an ion and further electrons which are then accelerated in opposite directions by the field. A workpiece positioned in the plasma, generated in this manner, is bombarded by these particles. Particles, for example may include oxygen ions, thereby enhancing the probability of oxidation of surface contaminants. Also, other gases, such as aldehydes, have been used for sterilization. Others have used argon or nitrogen to effect a surface abrasion.

One example of such a system is shown in U.S. Pat. No. 4,207,286 in which a coil, wound about a low pressure chamber is connected to a radio frequency signal generator to subject the chamber to an electromagnetic, alternating field at RF frequencies. Such a glow discharge induced by an RF electromagnetic field has also been used for the deposition of a film upon the surface of a workpiece, such as illustrated in U.S. Pat. No. 4,632,842. Yet other plasma/glow discharge treatment systems are illustrated in U.S. Pat. Nos. 4,348,357 and 4,656,083.

In an article entitled "Implant Surface Preparation" by Baier and Meyer, which appeared in Volume 3, No. 1, 1988 issue of *The International Journal Of Oral & Maxillofacial Implants*, the authors review various cleaning methods and give the reasons that they are necessary and conclude that glow discharge treatment shows the great promise for prosthetic dental devices.

In addition to bombardment with particles from a glow discharge plasma, others have proposed the irradiation of in U.S. Pat. No. 3,864,081. Ultraviolet systems often use mercury vapor lamps as the most effective way to sterilize.

In U.S. Pat. No. 3,876,373 workpieces are sterilized using reactive gases at low energies, creating a plasma discharge at sonic frequencies. This patent not only uses reactive gases but also seeks a resonant effect upon the living microorganisms. The difficulty with the low energy use of reactive gases at sonic frequencies is that the biological effectiveness of utilizing specific resonant frequencies to destroy microorganisms is not sufficiently proven or reliable and the use of reactive gases imposes dangers to human operators and problems with safely handling these reactive gases.

In the typical radio frequency apparatus a coil is wrapped around the low pressure chamber and a current is applied to the coil which alternates at a radio frequency. The current creates an electromagnetic field inside the chamber which ionizes the gas and creates the electron/ion plasma. This causes electrons to flow in a circular pattern with positive ions and electrons flowing in opposite directions. Each time the field reverses the direction of these particles reverses. The field pattern of these particles has the greatest particle motion or energy near the outer wall of the chamber.

Such RF units raise problems, including impedance matching, frequency stability, and the generation of a non-uniform plasma flow within the chamber. Impedance mismatching occurs when a conducting target placed in a chamber is sufficiently large to effect the RF currents. While automatic matching circuits can alleviate this problem, the mismatch can be so significant as to cause either automatic shut-down of the equipment or to burn out the power circuitry. Frequency stability is important. It is regulated by a governmental agency to prevent interference with other equipment operating at radio frequencies.

Because they operate at radio frequencies, the electromagnetic energy applied to the coil which surrounds the chamber is partially radiated into the atmosphere. This means that the voltage and current applied to the coil do not bear a sufficiently accurately known or constant relationship to the particle currents within the plasma to enable them to be used to control the process. Additionally, these emissions cause shielding and radio emission problems which can interfere with other uses of the frequency spectrum.

Furthermore, in coil driven RF systems the plasma is formed in a thin circular pattern within the chamber, leaving a relatively large, central cold space in which there is relatively little particle motion with relatively low energy particles to collide with the workpiece being treated. Thus, in the RF systems the effective work area is confined to a thin, cylindrical, circumferential layer requiring that the workpiece not extend inwardly beyond this layer, therefore limiting the size of the chamber and the workpieces.

Thus, in summary, the prior art teaches that, in the use of a glow discharge plasma for the treatment of workpieces, one uses sonic frequencies to effect the microbiological organisms and uses radio frequencies in order to eliminate electrodes from the chamber. It also teaches the use of biologically active gases. However, since biologically active gases pose handling problems and the use of RF energy poses control problems, there is therefore a need for a cleaning technique and system which overcomes these problems to provide for the effective cleaning of the workpieces under suitable control in order to optimize the cleaning effectiveness and minimize the time and equipment required for that effective cleaning.

BRIEF DESCRIPTION OF INVENTION

These and other objects of the invention may be accomplished by utilizing ultrasonic frequencies, above the sonic spectrum and below the radio frequency spectrum. This provides reduced acoustical wavelength structure and eliminates the RF radiation problems. Importantly, it also enables the implementation of improved control because, in the absence of energy radiation, the electrode currents accurately represent the plasma currents. This is enhanced further by applying the alternating voltage to electrodes formed as a pair of spaced conductive, interfacing panels mounted within the low pressure chamber to define a three-dimensional cleaning space in the volume between these panels. This provides an enlarged cleaning region to allow larger workpieces to be cleaned than is permissible in the conventional RF plasma treating systems.

The gas is preferably, predominantly an inert gas, such as argon, though it may contain an active, biologically safe gas, such as oxygen.

In an ultrasonic unit with internal electrodes the particle flow pattern is essentially line-of-sight in the volume between the electrodes. A uniform pattern of flow in the volume between the panels is maintained by operating in the abnormal glow region to provide a uniform cleaning space between the electrodes.

Yet another advantage of ultrasonic frequencies is the fact that the ordinary dimensions of a typical, low pressure cleaning chamber are substantially larger than the acoustical wavelength at the ultrasonic frequencies. This means that the ionized particles which are of a molecular size and therefore are similarly sized to air particles, provide a transmission medium similar to that of an air medium transmitting sonic waves by a similar mechanism. Since the dimensions within the chamber, between the electrodes, the walls, and the workpieces are many acoustical wavelengths long at ultrasonic frequencies, the operation is not significantly disturbed or altered by or sensitive to the size or placement of the workpieces within the chamber.

Figure 1:
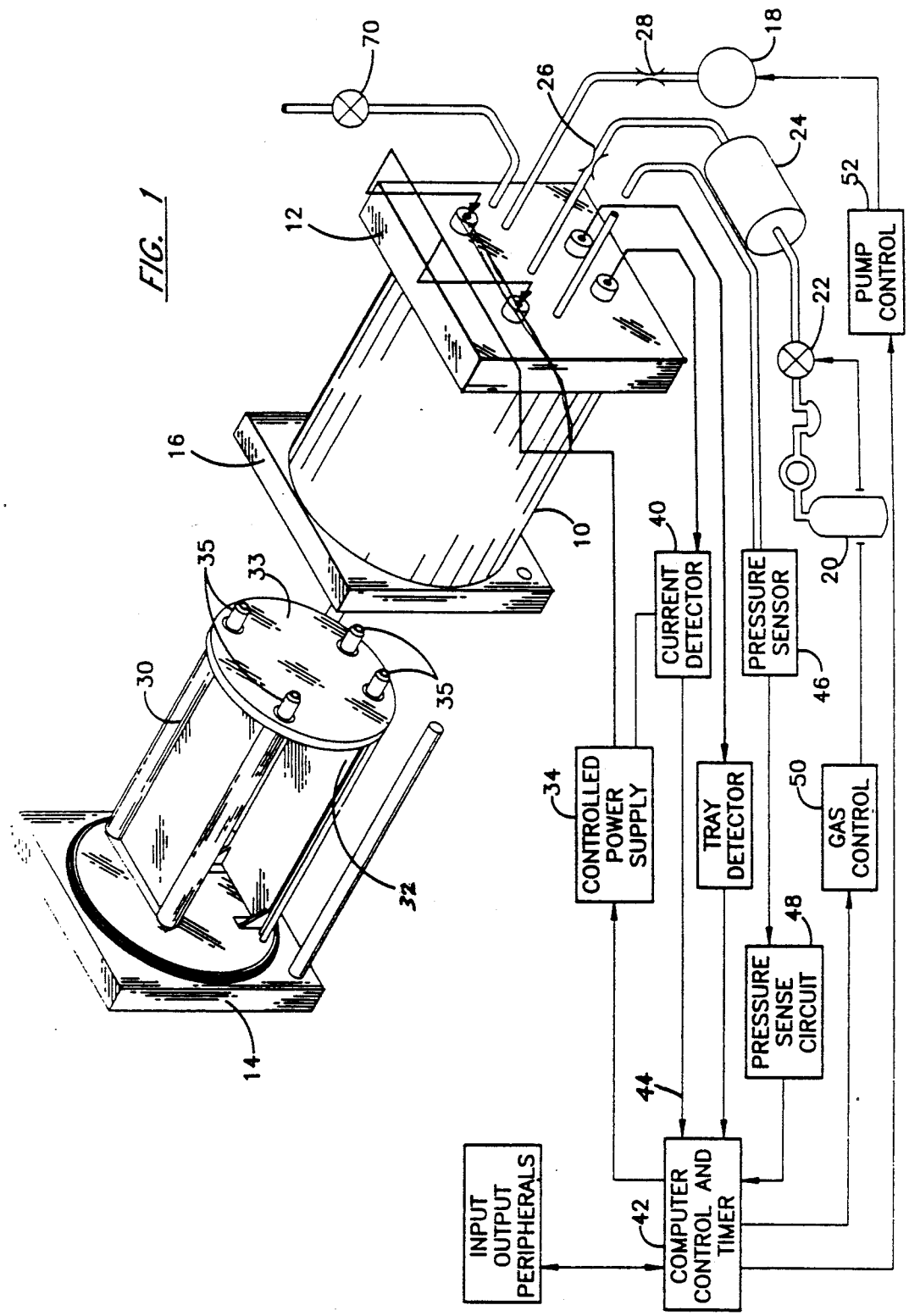
FIG. 1 is a diagrammatic view showing the mechanical structure of the invention in perspective and illustrating the control circuit as a block diagram.

In describing the preferred embodiment of the invention which is illustrated in the drawings, specific terminology will be resorted to for the sake of clarity. However, it is terms so selected and it is to be understood that each specific term includes all technical equivalents which operate in a similar manner to accomplish a similar purpose. For example, the word connected or terms similar thereto are often used. They are not limited to direct connection but include connection through other circuit elements where such connection is recognized as being equivalent by those skilled in the art.

DETAILED DESCRIPTION

FIG. 1 illustrates a cylindrical, low pressure chamber 10 having a manifold 12 sealed to one end and a removable, sealable closure 14 which can be moved against the opposite end 16 of the chamber 10 and sealed against it to seal the chamber against the entry of ambient atmosphere. A vacuum pump 18 is connected through the manifold 12 in communication with the interior of the chamber. Preferably an orifice 28 is interposed between the pump 18 and the interior of the chamber 10 in order to regulate the flow rate of gas which is pumped from the chamber by the pump 18. The purpose of the pump 18 is to remove gas from the chamber 10 in order to reduce its pressure.

A manually actuated air relief tube and valve 70 is also connected into communication with the low pressure chamber 10 to permit an operator to vent the chamber 10 to the atmosphere after a cleaning operation is completed so that its pressure can be equalized with the atmosphere.

The source 20 of ionizable gas, preferably an inert gas such as argon, is connected through a solenoid controlled valve 22 and through the manifold 12 into communication with the interior of the chamber 10.

Preferably a reservoir 24, which is a substantially enlarged volume, and a restrictive orifice 26 are serially interposed between the valve 22 and the chamber 10. The reservoir is interposed between the valve 22 and the orifice 6. This permits the reservoir to be charged with brief, relatively higher pressure pulses of ionizable gas to raise its pressure to a relatively high pressure while subsequently permitting the gas to trickle into the chamber through the orifice 26 at a relatively slow controlled rate.

A pair of spaced, conductive, interfacing panels 30 and 32 form electrodes to which the high voltage, ultrasonic power supply 34 is electrically connected. These panels have a length and width to define a three-dimensional cleaning space in the volume between them. Preferably the lower electrode panel 32 is mounted directly upon the closure 14 and is formed as a horizontally oriented tray. This tray may be used to support a workpiece or preferably to support a raised grille or other suitable workpiece support surface above the surface of the tray. The workpiece is preferably held away from the electrode because the plasma cloud decreases in density within one mean free path from the electrode. The workpieces are supported above the tray away from the electrode in a region where a uniform particle activity occurs. This construction also permits the workpiece support to be removed from the chamber along with the closure 14 as a unitary body so that it may be conveniently loaded or unloaded with the workpieces. Preferably the electrodes are constructed of titanium because titanium is biocompatible. A molecular transfer from the electrodes may occur during product handling.

It is also desirable to mount the upper electrode 30 to an insulating support wall 33 which is in turn mounted to the lower tray electrode 32. In this manner both electrodes are removed from the low pressure chamber 10 with the closure 14 so they are accessible for servicing. Each electrode panel 30 and 32 is supported by a pair of horizontal support rods which protrude from the aft end of the vertical support wall 33 to form male electrical connectors 35 which insert into mating female electrical connectors, not visible, formed in the interior wall of the manifold 12. These in turn are connected to the electrical connections illustrated in FIG. 1.

An electrical current detector 40 is connected between the power supply 34 and the electrode 32 to detect the power supply current, which at ultrasonic frequencies is identical to the plasma current between the electrode 30 and 32. The current indicating output 44 from the current detector 40 is connected to the computer control and timer circuit 42 for use in control of the apparatus.

It is desirable in operating the preferred embodiment of the invention to accumulate the total time period during which plasma current flows because cleaning of the workpiece only occurs during plasma current flow. As will be described below, the unit is preferably operated in a cyclical manner with periodic intervals during which plasma current does not flow. This timer means may be a separate timing accumulator or preferably is simply accomplished by the computer control and timer 42 using standard software techniques.

A pressure detecting means 46 is connected in fluid communication with the chamber 10 to sense the chamber pressure. Its output is connected to a pressure sensing circuit 48 which in turn is connected to the computer control and timer 42 for providing chamber pressure data to the computer control and timer 42. The gas source control valve 22 is also connected to a gas control circuit 50 which in turn is connected to an output from the computer control and timer 42 so that the computer can control, by turning on and off, the solenoid valve 22 to control the injection of the inert gas from the gas supply 20, preferably in accordance with the method of the present invention. Similarly, the vacuum pump 18 is connected through a pump control circuit 52 to another output of the computer control and timer 42 so that the computer can control the vacuum pump 18 by turning it on and off preferably in accordance with the method of the present invention.

In the operation of the embodiment of the invention illustrated in FIG. 1 workpieces, such as dental implants being prepared for surgical insertion within a patient, are positioned upon the workpiece support platform or grille which rests upon the lower electrode tray 32. The purpose of cleaning is to remove surface contaminants, such as water.

After the electrodes carrying the workpieces are inserted axially into the cylindrical low pressure chamber 10 and the closure 14 is sealed against the end 16 of the chamber 10, operation of the computer control and timer 42 is initiated. The first step is the evacuation of the ambient air from within the low pressure chamber 10. While continuously monitoring and detecting the chamber pressure, air is evacuated until the pressure descends to a first selected gas pressure, such as 0.6 torr. When the computer control senses that the selected gas pressure has been reached, it actuates the gas solenoid valve 22 to inject a selected ionizable gas, such as argon, into the chamber in order to effect an atmosphere which is predominantly composed of the selected gas. This may be accomplished, for example, by injecting the gas until the gas pressure exceeds a higher pressure such as, for example, exceeds 1.2 torr. Preferably the pump 18 continues to exhaust gas from the low pressure chamber 10. When the pressure falls to a reduced pressure, such as, for example, 0.8 torr, which is sensed by the computer through the pressure detector 46, the computer actuates the controlled power supply 34 to apply the voltage to the electrodes and initiate the glow discharge. The power supply may, for example, apply 500 volts in its normal current operating range.

It is important that the voltage not be applied to initiate generation of the plasma until the pressure is sufficiently low that the gas molecule density in the chamber will be low enough to maintain the plasma essentially in an abnormal glow state within the chamber and particularly in the cleaning space. As is known to those skilled in the art, abnormal glow occurs when essentially all of the gas molecules must be ionized to provide carriers for the current. Typically in abnormal glow the ions are multiply ionized, that is more than one electron is freed from most ions by the collisions. In this condition the plasma is uniformly distributed across the electrodes and therefore through the cleaning space between the electrodes.

If there were a higher density of gas molecules, the glow discharge would be in the normal glow region so that the total plasma current could be carried by ionization of fewer than all the gas molecules. Initiating such glow discharge at a pressure which is too high would cause the plasma to form in a concentrated manner in a relatively small region between the electrodes, rather than being distributed over the entirety of the electrodes. Such a discharge would cause hot spots, concentrating all of the energy in a relatively small area and thus possibly damaging the electrodes and more importantly the workpieces positioned in that discharge area between them. Thus, it is important that gas is pumped from the chamber, at least when the gas pressure exceeds a selected maximum gas pressure which would result in normal glow discharge. The pressure should never be permitted to rise high enough to allow normal glow discharge. Preferably, the pump is operated continuously and the inert gas is injected in periodic cycles as described below.

Another advantage of using the lower pressure and operating in the abnormal glow region is that the low molecular density results in a longer mean free path for the carriers. As a result, the cleaning of the workpieces is more uniform and is not so dependent upon electrode or workpiece contours, size or shape.

After the glow discharge is initiated, the computer control and timer 42 then monitors the electrode current through the current detector 40. Unlike radio frequency units, this current is an accurate indication of the plasma current between the electrodes which is active in cleaning the workpieces. The magnitude of the initial electrode current is stored and represents the maximum electrode current. As glow discharge and simultaneous cleaning occur and the vacuum pump 18 continues to pump, the gas pressure will relatively, slowly decrease because of the removal of gas molecules by the pump and therefore the density of current carriers in the plasma will slowly decrease. Typically, the maximum current is on the order of 100 milliamperes. When the current falls to below a selected threshold proportion of the maximum electrode current, such as, for example, to below two-thirds of the stored maximum electrode current, additional gas is injected into the chamber by a brief opening of the solenoid valve 22.

To accomplish the injection of the additional gas, the computer control and timer 42 turns off the controlled power supply 34 and turns on the solenoid valve 22 to inject the pulse of gas. We have found that typically when the current falls to approximately two-thirds of the maximum current value the pressure has fallen to approximately 0.35 torr. The computer control and timer 42 and the solenoid are designed to inject approximately sufficient gas to raise the pressure by 1 torr to approximately 1.35 torr. During the gas injection, the controlled power supply is turned off when the pressure is measured because otherwise the presence of the plasma would distort the pressure reading. If the pressure maximum is not exceeded, the power supply is then glow discharge in the abnormal region.

It is, of course, possible to utilize a variable control valve and modulate the flow rate of inert gas from the gas supply 20 into the low pressure chamber 10. However, we have found it more cost effective to provide a pulse of gas into the reservoir 24 and permit it to slowly bleed through the gas orifice 26 into the low pressure chamber 10. The process is repeated in a cyclical manner which is illustrated in FIGS. 2, 3, and 4.

Figure 2:
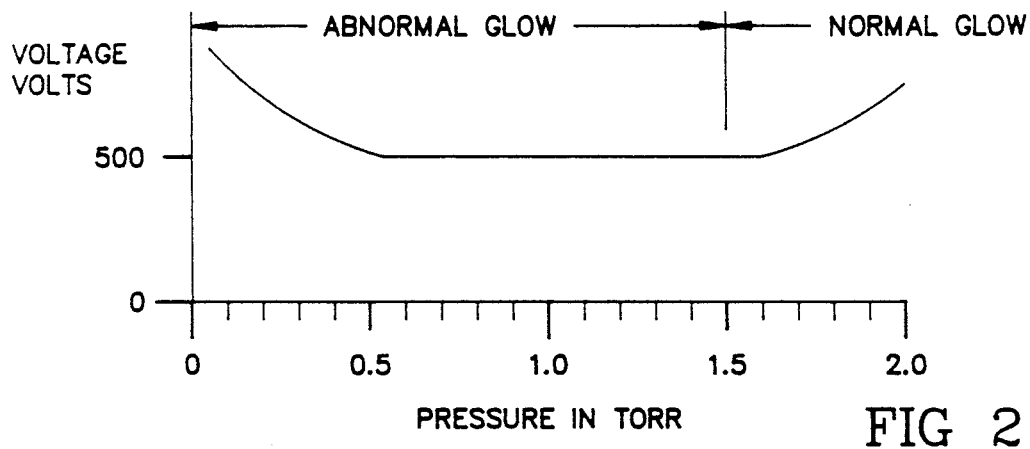
FIGS. 2, 3, and 4 are graphs illustrating the operation of embodiments of the invention.

FIG. 2 illustrates the voltage variation in a typical unit as a function of gas pressure and shows that the boundary between the abnormal glow and normal glow regions occurs approximately at 1.5 torr. FIG. 3 illustrates the electrode current which occurs as a function of pressure over the same pressure range. It shows that at very low pressures below approximately 0.35 torr, the voltage increases and the current decreases as a result of the increased impedance of the plasma arising from the reduction in carriers within the plasma due to the low molecular density of gas molecules. At higher gas pressures the glow discharge will be in the normal glow region in which increased gas molecule density will cause normal glow. The voltage increases and current decreases at higher pressure because plasma impedance increases so, a higher voltage is required to maintain ionization.

Figure 3:
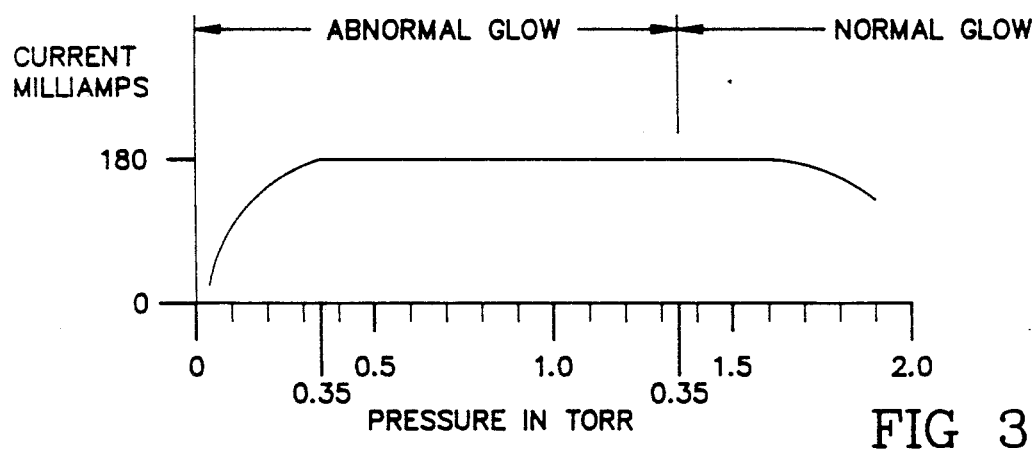

FIG. 3 illustrates the periodic cycling to maintain the gas pressure in the range which maintains abnormal glow discharge. The gas supply 20 may, for example, typically be at a pressure of 150 PSI. Gas is supplied from the gas supply valve at a pressure which is suitably reduced, for example 0.5 PSI, by conventional regulators which may be included within the gas supply in the conventional manner. It provides the brief pulses of gas illustrated in FIG. 3. This causes the reservoir to be periodically and rapidly charged and thereafter slowly permit the gas from the reservoir to trickle out into the low pressure chamber 10. As a result, the pressure within the low pressure chamber 10 relatively more slowly increases and then gradually decreases until the current again falls below the selected level of approximately two-thirds of the maximum current. Typically, at that point the pressure has fallen to 0.35 torr when the next pulse of gas from the gas supply 20 is initiated.

Figure 4:
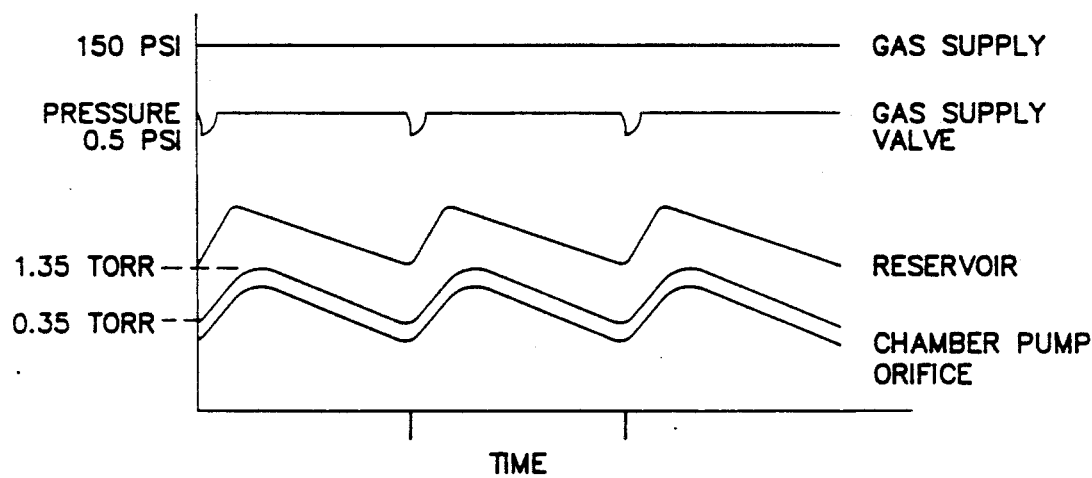

Each time during the repetitive, periodic cycle, illustrated in FIG. 4 that the electrode voltage is reapplied following a gas injection, the initial, maximum electrode current is again measured. If it exceeds the previously stored maximum electrode current, the new electrode current is stored as the maximum electrode current. Thereafter the cycle is repeated by turning off the voltage and injecting additional gas when the current falls to the selected proportion of the new maximum electrode current, such as two-thirds of the new maximum electrode current.

Because cleaning of the workpieces occurs only during current flow through the plasma, the total time of electrode current flow is accumulated. After the accumulated cleaning time is equal to a preselected, desired cleaning time, which may, for example, be preset by an operator, the procedure is discontinued. Thereafter the operator may open the air relief hand valve 70 to permit air to reenter the chamber. The closure 14 may then be opened and the cleaned workpieces removed and utilized.

Additionally, it is desirable to monitor the pressure each 12 seconds to be certain that a fault has not occurred and the pressure has not exceeded the maximum pressure at which abnormal glow discharge occurs. For the reasons stated above, the application of voltage to the electrodes is disconnected if the pressure is found to have risen above this limit where normal glow discharge would occur. This is checked periodically, such as every 12 seconds, and in addition is also checked just before reapplication of the voltage and reinitiation of the cleaning by the plasma after each gas injection during the cyclical operation illustrated in FIG. 4.

It is also desirable for some applications to utilize a gas which is a mixture of ten percent oxygen and ninety percent argon. The small amount of oxygen enhances the oxidation of any contaminants while posing no danger since that is less oxygen than found in the atmosphere.

When the high voltage drives the upper electrode 30, negative with respect to the lower electrode tray 32, the tray becomes the anode and is bombarded by electrons. When the high voltage reverses the cathode is bombarded by the positive ions. During abnormal glow the bombardment of metal surfaces by positive ions is high, creating high values of the secondary emission and heating of the surface. This bombardment by the molecules abrades the surface of the workpieces to knock off surface contaminants. Reducing the pressure increases the mean free path of the electron and therefore increases the energy which they obtain before striking a surface. The mean free path of electrons varies from about 0.3 millimeters at a pressure of 1.2 torr, up to about 2.2 millimeters at 0.2 torr.

The ultrasonic frequency range of preferred operation is preferably within the range of 20 Khz to 50 Khz. It is desirable that the frequency be sufficiently high that acoustic effects in the ordinary dimensions for such cleaning devices and workpieces be eliminated. The frequency should not be so high that any significant electromagnetic radiation would occur which would interfere with radio frequency uses of the spectrum, such as for communication. We prefer to operate at 23.5 Khz.

While certain preferred embodiments of the present invention have been disclosed in detail, it is to be understood that various modifications may be adopted without departing from the spirit of the invention or scope of the following claims.

I claim:

1. An apparatus for abrading contaminants from the surface of a workpiece and comprising:
 (a) a low pressure chamber having a sealable closure;
 (b) pumping means connected to the chamber for removing gas;
 (c) a source of ionizable gas connected to the chamber;
 (d) a set of spaced conductors forming electrodes mounted within the chamber and having a length and width extent to define a three-dimensional cleaning space in the volume defined between them;
 (e) a power supply having its output connected to the electrodes for supplying alternating current to the electrodes at an ultrasonic frequency and at a sufficient voltage and current to ionize gas within the chamber to form a plasma; and
 (f) a workpiece support means mounted in the cleaning space.

2. An apparatus in accordance with claim 1 wherein the gas is an inert gas.

3. An apparatus in accordance with claim 1 wherein said workpiece support means is supported upon the closure.

4. An apparatus in accordance with claim 3 wherein one of said electrodes is mounted to the closure and is formed as a horizontally oriented tray to support a workpiece.

5. An apparatus in accordance with claim 1 or 2 or 3 or 4 wherein the electrodes are titanium.

6. An apparatus in accordance with claim 1 or 2 or 3 or 4 wherein a current detector is connected to the power supply to detect the plasma current for use in control of the apparatus.

7. An apparatus in accordance with claim 6 and further comprising:
(a) timer means connected to the current detector for accumulating the total time period of plasma current flow;
(b) a pressure detector in fluid communication with the chamber for sensing chamber pressure;
(c) a gas source control valve; and
(d) digital data processing means having inputs connected to the timer means, pressure detector and current detector and outputs connected to the pumping means, power supply means and gas source control valve for controlling their actuation in accordance with a programmed algorithm.

8. An apparatus in accordance with claim 7 wherein a reservoir and a restrictive orifice are serially connected in communication between the gas source control valve and the chamber, the reservoir being interposed between the valve and the orifice for charging the reservoir with the ionizable gas and permitting it to trickle into the chamber through the orifice.

9. An apparatus in accordance with claim 8 wherein a restrictive orifice is interposed between the pump and the chamber for limiting the gas exhaust flow rate.

* * * * *